United States Patent [19]
Nestor et al.

[11] Patent Number: 5,234,835
[45] Date of Patent: Aug. 10, 1993

[54] PRECALIBRATED FIBER OPTIC SENSING METHOD

[75] Inventors: James R. Nestor, Northborough, Mass.; Bennett L. Hauenstein, Nashua, N.H.

[73] Assignee: C.R. Bard, Inc., Murray Hill, N.J.

[21] Appl. No.: 766,021

[22] Filed: Sep. 26, 1991

[51] Int. Cl.$^5$ ............................................. G01N 21/00
[52] U.S. Cl. ..................................... 436/11; 128/633; 128/634; 422/82.06; 436/8; 436/172
[58] Field of Search ................. 436/8, 11, 172; 422/1, 422/82.06–82.09; 128/634, 633

[56] References Cited

U.S. PATENT DOCUMENTS

| | | |
|---|---|---|
| 3,504,521 | 4/1970 | Luckers . |
| 4,481,804 | 11/1984 | Eberhard et al. ............... 204/406 X |
| 4,752,115 | 6/1988 | Murray, Jr. et al. . |
| 4,800,886 | 1/1989 | Nestor ................................. 128/634 |
| 4,861,727 | 8/1989 | Hauenstein et al. ................. 436/136 |
| 4,863,016 | 9/1989 | Fong et al. ........................... 206/210 |
| 4,941,308 | 7/1990 | Grabenkort et al. ................. 53/425 |

FOREIGN PATENT DOCUMENTS

| | | |
|---|---|---|
| 0221357 | 6/1987 | European Pat. Off. . |
| 0271304 | 6/1988 | European Pat. Off. . |
| 0351516 | 5/1989 | European Pat. Off. . |
| 0074498 | 3/1983 | Fed. Rep. of Germany . |

OTHER PUBLICATIONS

Gehrich et al., "Optical Fluorescence And Its Application To An Intravascular Blood Gas Monitoring System," IEEE Transactions On Bio-Medical Engineering, vol. 33, No. 2, Feb. 1986, pp. 117–132.

Tusa et al., Optical Fibers in Medicine II, Proceedings of SPIE Int'l. Soc. for Opt. Eng., vol. 713, 1986, pp. 137–143.

Spectramed Inc.—Company Report.

*Primary Examiner*—Jill A. Johnston
*Attorney, Agent, or Firm*—Wolf, Greenfield & Sacks

[57] ABSTRACT

A precalibrated sensing system for determining a blood parameter such as the partial pressures of oxygen ($pO_2$) and carbon dioxide ($pCO_2$), and the negative logarithm of hydrogen ion activity (pH). A dry sensor is provided which may be calibrated in the factory, packaged, sterilized and stored, without requiring recalibration prior to use.

8 Claims, 6 Drawing Sheets

PRECALIBRATED FIBER OPTIC SENSING METHOD

FIELD OF THE INVENTION

This invention relates to an optical sensing system for measuring a parameter of the blood, such as the partial pressure of a blood gas or blood pH, and in particular to a system which can be calibrated in the factory and stored for extended periods without requiring recalibration prior to use.

BACKGROUND OF THE INVENTION

Arterial blood gas and pH values are of primary importance in the management of critical care and surgical patients. The three parameters of interest are the partial pressures of oxygen ($PO_2$) and carbon dioxide ($PCO_2$), and the negative logarithm of hydrogen ion activity (pH). These three parameters are a good indication of a patient's cardiac, respiratory and circulatory functioning.

The standard technique for measuring blood gases involves invasive sampling from the radial artery, with analysis of the blood sample conducted in a diagnostic laboratory, usually some distance from the patient. The results are typically obtained 10-20 minutes after the sample has been taken, during which time the patient's blood gas levels may have changed.

This lack of timely results and the use of single-point sampling are problems which make it difficult to determine current patient status and to recognize trends. Also, there is a source of potential error resulting from the extensive sample handling from bedside to laboratory. The desire for improved patient care by eliminating these drawbacks has created the need for an improved blood gas monitoring system.

Among the suggested improvements is a continuous blood gas monitoring system utilizing an invasive probe placed directly in an artery having electrical or optical sensing means. The in vivo electrode probes have not been generally accepted because of the danger of using electrical currents in the body and the difficulty of properly calibrating the electrodes.

In a fiber optic system, light from a suitable source travels along an optically conducting fiber to its distal end where it undergoes some change caused by interaction with a component of the blood to be measured, or interaction with a material contained in the probe tip which is sensitive to the component of the blood, and the modified light returns along the same or another fiber to a light-measuring instrument which interprets the return light signal. This system offers several potential benefits. A fiber optic sensor is safe, involving no electrical currents in the body. Optical fibers are very small and flexible, allowing placement in the very small blood vessels of the body. The materials used, i.e., plastic, metal and glass, are suitable for long-term implantation. However, although the potential benefits of an indwelling fiber optic blood gas sensor have long been recognized, they have not yet been realized in the viable commercial product.

Optical blood gas sensors based on fluorescent dyes are described in J. Gehrich et al., "Optical Fluorescence And Its Application To An Intravascular Blood Gas Monitoring System," IEEE Transactions On Biomedical Engineering, Vol. BME-33, No. 2, February 1986, pp. 117-132. Fluorescence is a type of photo-luminescence in which light energy is emitted when an electron returns from an excited singlet state to the ground state. Phosphorescence is a longer-lived type of photoluminescence in which the release of energy is from the triplet state. Because fluorescent and phosphorescent dyes emit light energy at a wavelength different from that at which they absorb the excitation energy, a single optical fiber can be used to both deliver and receive light energy from the sensor dye. Use of the single fiber reduces the diameter of the sensor probe, an important consideration in enabling placement of the sensors in an artery or vein. A blood oxygen sensor based on a phosphorescent lanthanide complex is described in U.S. Pat. No. 4,861,727 to Hauenstein et al. Hauenstein et al. describes an oxygen-quenchable luminescent lanthanide complex disposed in a solid polymeric matrix at the distal end of an optical fiber. A non-oxygen quenchable reference complex is also provided to continuously monitor the source radiation and losses in the sensor system.

Another type of optical sensor is based on the principle of optical absorption. In this case, a sensor disposed in the blood is permeated by the component of interest and an optical signal passing through the sensor is absorbed by the component in direct proportion to the concentration of the component, such that the energy signal which exits the sensor is reduced in an amount proportional to the concentration of the component in the blood. A carbon dioxide ($CO_2$) sensor of this type is described in U.S. Pat. No. 4,800,886 to Nestor in which a fixed-length axial segment is provided at the end of an optical fiber, which segment is permeable to $CO_2$.

The challenges in designing a fiber optic blood gas sensor include the selection of a sensing material which has the proper absorption and emission wavelength characteristics, is non-toxic, is capable of attachment to an optical fiber (or to a suitable matrix), and has sufficient intensity (signal strength) and sufficient intensity variation over the physiological measurement range (sensitivity and range) to adequately follow physiological changes of the blood gas parameters. The sensing material must also not be affected by drugs or blood components, and must be stable enough to maintain accuracy for up to three days (72 hours) of use. Furthermore, since it is desirable to provide a disposable product, consideration must be also be given to the cost and shelf life.

A principal difficulty with the invasive blood gas systems currently under development concerns the time-consuming, costly and error-prone calibration process required just prior to use. As described in C. Mahutte, et al., "Progress In The Development Of A Fluorescent Intravascular Blood Gas System In Man," Journal of Clinical Monitoring, Vol. 6, No. 2, April 1990, pp. 147-157, the sensors now under development require a 20-minute calibration procedure which is done at the patient's bedside just prior to use. During calibration, the sensor is placed in at least two buffered solutions, each containing different precisely known concentrations of oxygen and carbon dioxide. Based on the sensor response to these standard solutions, calibration constants are determined which enable conversion of the measured intensity to an actual blood gas value by accounting for the bias between the measured and actual values and a temperature correction (in that $CO_2$ and $O_2$ measurements are both temperature dependent).

There are a number of problems with the standard calibration technique. The calibration solutions must be highly uniform to provide consistent results. The solutions are typically unstable and thus are prepared only as needed or prepackaged in glass ampules. The ampules require careful handling during the calibration process to avoid breakage. Shelf life problems, i.e., change of chemistry, separation, etc., may be encountered with prepackaged solutions that are stored over a period of time. There is a danger of contamination. The calibration equipment is cumbersome and costly, including two glass bottles, each with different but precisely controlled values of oxygen and carbon dioxide, tubing, pressure regulators, flow restrictors and solenoid valving as necessary to select the desired gas mixtures and control the flow within required ranges. Trained personnel are generally required to perform this procedure at the bedside. The calibration accuracy depends upon the strictness to which the calibration protocol is followed. Requiring this procedure at the patient's bedside, as opposed to in the factory where the product is manufactured, increases the likelihood of errors being made in the calibration procedure.

If the calibratable device is to be stored over a period of time, the device is most easily stored in the dry state to avoid problems arising from the storage of a moist device. In particular, the dry state is far more amenable to the requirement that the device be rendered sterile and held in a sterile state throughout its useful life. However, bringing the sensing component of the device from a dry to an equilibrated wet state often requires hydrating the sensor over an extended period of time. While it has been suggested to sell the sensor packaged in a calibration cuvette which contains the calibration solution (see J. Gehrich et al. at p. 124, and C. Mahutte et al. at p. 149), this leads to rather elaborate and expensive packaging techniques and does not eliminate the need for a bedside calibration.

Finally, it is generally required with the known devices that calibration be done just prior to placement in the patient, which means within a few minutes. Thus, if some unexpected delay is encountered, the entire calibration procedure may have to be redone. Further, calibration just prior to placement may jeopardize device sterility and requires that the calibration be performed in a sterile environment. Also, after placement in the patient, the known devices may only be stable for less than 24 hours, before requiring recalibration. It would be desirable to have a device remain stable up to 72 hours after placement.

It is an object of the present invention to provide an optical sensor which can be calibrated in the factory prior to shipment to the customer, and which does not require recalibration prior to use.

A further object is to provide a precalibrated sensor which can be stored in a dry condition, and does not require packaging and storage in a calibration solution.

A still further object is to provide a sensor which can be calibrated and then sterilized, wherein the sterilization procedure does not substantially effect the calibration.

SUMMARY OF THE INVENTION

In accordance with this invention, a precalibrated optical sensing system is provided for sensing a parameter of the blood. The system includes a stable optical sensor in solid form, and an associated set of calibration data for the sensor stored on a recording medium. The sensor may be stored outside of any calibration medium and has a shelf life of at least about 24 hours without requiring recalibration. Preferably, the sensor will remain stable following calibration and prior to placement in a patient for at least about 30 days. Furthermore, once placed in the patient, the sensor preferably remains stable for greater than 24 hours, and preferably for at least about 72 hours.

The invention further comprises a method of providing a precalibrated optical sensor including the steps of providing a stable optical sensor in solid form for sensing a blood parameter, determining an associated set of calibration data for the sensor by exposing the sensor to at least one calibration medium, recording the calibration data on a recording medium, removing the sensor from the calibration medium, and storing the sensor and recording medium for at least 24 hours before use.

Preferably, the sensor includes an optical transmission medium, such as an optical fiber. One or more of these fibers, with different sensing materials on their distal ends for measuring different blood parameters (i.e., the partial pressures of oxygen and carbon dioxide, and the blood pH), may be combined into a single probe positionable within the radial artery for continuous blood gas monitoring. The sensors may be luminescent or absorptive sensing materials which alter the excitation energy signals sent down the fibers based upon the amount of the analyte ($O_2$, $CO_2$ or hydrogen ion) in the blood. The sensing material may be applied directly to the optical fiber alone or in combination with a matrix, such as a polymeric matrix. The sensors are calibrated in the factory and then subsequently sterilized and packaged before being shipped to the customer. The sensors may be stored in a dry condition, apart from any calibration solution, for an extended period prior to use without requiring recalibration.

A preferred oxygen sensor comprises an oxygen-quenchable luminescent lanthanide complex which may be disposed in a solid polymeric matrix at the distal end of an optical fiber. For example, a lanthanide complex consisting of terbium ions complexed with at least one Schiff base or $\beta$-diketone ligand emits a narrow-line luminescence of relatively long lifetime and sufficient sensitivity when disposed in a solid polymeric matrix. This complex has been found to be stable over relatively long periods and its response is not substantially altered by sterilization.

A preferred carbon dioxide sensor comprises a fixed axial segment of a polymer permeable to $CO_2$ disposed at the distal end of an optical fiber. The intensity of light returning down the fiber is diminished in proportion to the concentration of $CO_2$ in the axial segment. Preferably, the fiber is made of a fluoride glass and the axial polymeric segment is silicone. The sensor has been found to be stable and may be sterilized following calibration in the factory.

DETAILED DESCRIPTION

Figure 1:
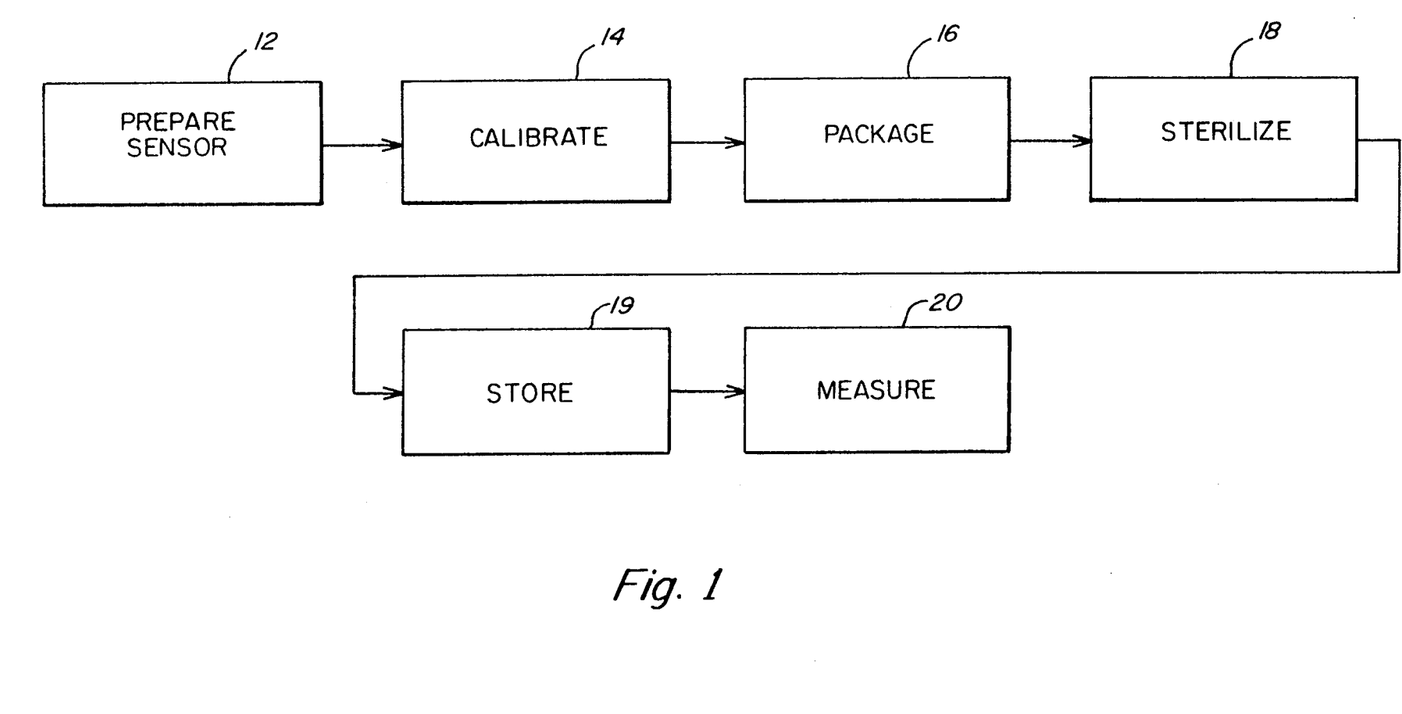
FIG. 1 is a block diagram illustrating the method of this invention for providing a precalibrated optical sensing system.

FIG. 1 illustrates in block format the method of this invention for providing a precalibrated optical sensing system. A first step 12 is preparation of the optical sensor, followed by calibration 14 of the sensor to obtain the associated calibration data. The sensor is then packaged 16 and sterilized 18. These steps are conducted at the manufacturing location. The sensor and calibration data are then stored 19 and shipped to the customer for use at some indeterminate later time to measure 20 a blood parameter of a patient. The sensor is sufficiently stable that its calibration data, taken prior to packaging, sterilization and storage, remains sufficiently constant to enable its use at a significantly later time, without requiring recalibration prior to use. This system is much simpler and more convenient for the user and less prone to errors in the calibration data because all of the time-consuming and skilled labor required for calibration is conducted in the manufacturing facility, as opposed to in the hospital at the patient's bedside just prior to use.

Figure 2A:
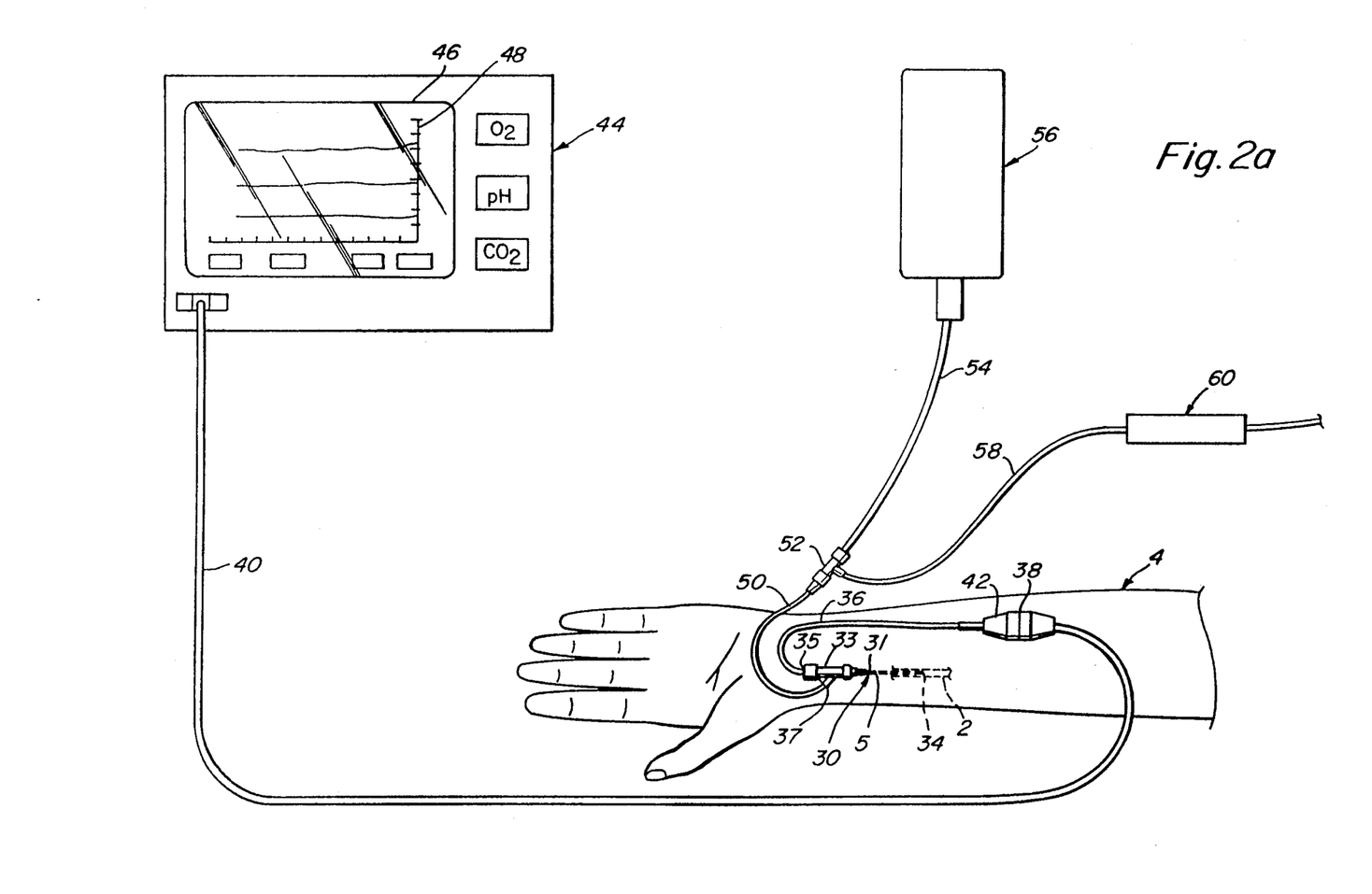
FIG. 2a is a diagram illustrating use of the precalibrated blood gas sensing system of this invention.
Figure 2B:
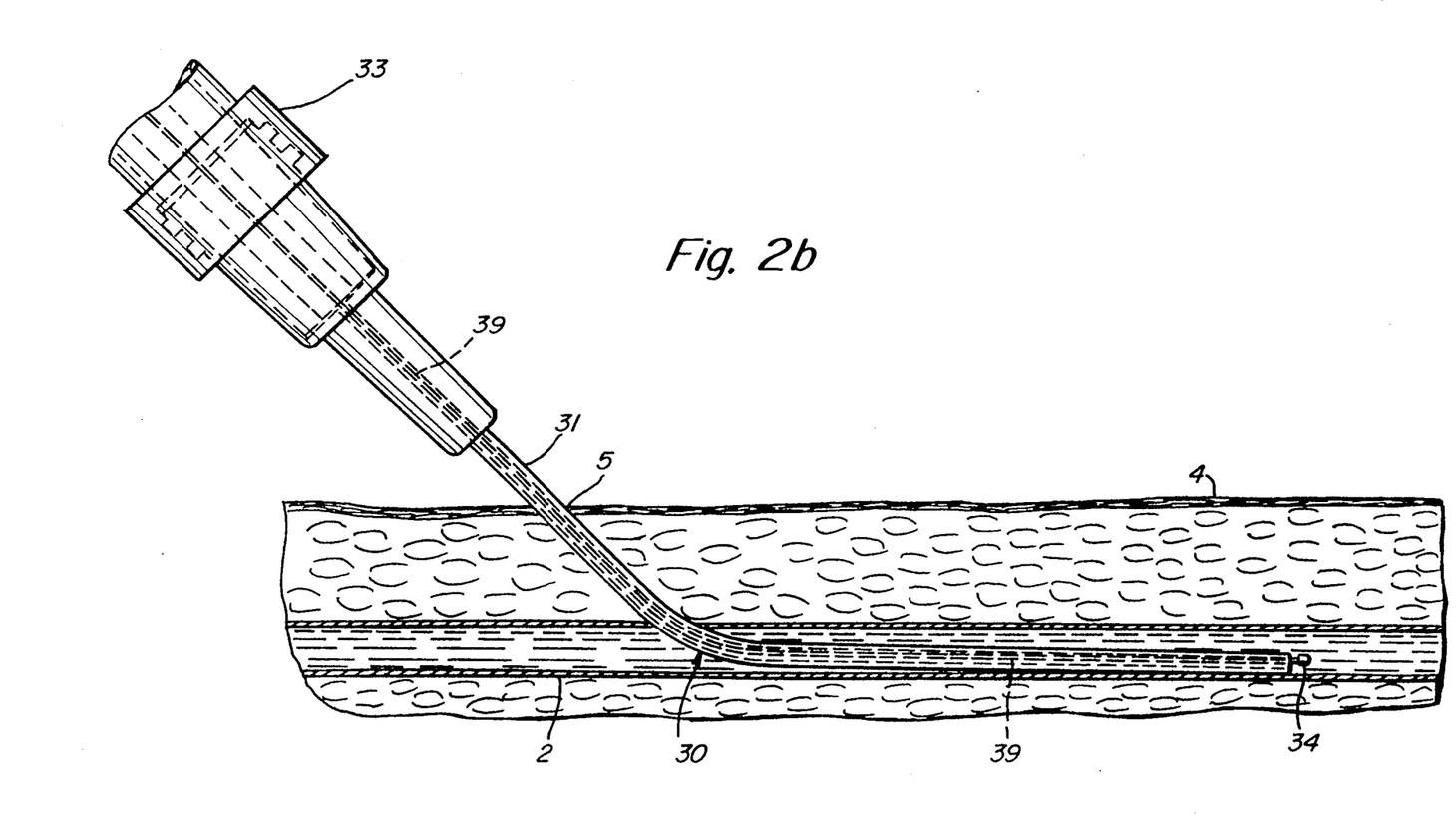
FIG. 2b is a sectional diagram showing placement of the sensor probe in the radial artery.

FIGS. 2a and 2b illustrate the use of a precalibrated system for continuous in vivo blood gas monitoring. An optical sensor probe 30 is positioned in a radial artery 2 of a patient's forearm 4. The indwelling portions of the probe 30 and introducer catheter 31 are positioned in the patient's radial artery 2 and exit through the skin from an insertion site 5. The probe includes at least one optical fiber 39 (FIG. 2b) having a sensor 34 at its distal end which is positioned in the artery, outside the distal end of the catheter 31. Moving proximally from the insertion site 5 (FIG. 2a), a proximal end of the introducer catheter 31 is attached to a Y-body fitting 33. The Y-body 33 has a main lumen and proximal port 35 through which the probe 30 passes, and a secondary side branch off the main lumen terminating at port 37, to which a fluid line 50 is attached. The fluid line 50 branches into two sections at a stop-cock connection 52, the first branch 58 being connected to a pressure transducer 60 for measuring the patient's blood pressure, and a second fluid line branch 54 being connected to a source 56 of fluid, such as a saline solution for flushing the system to prevent blood clotting. The outer probe sheath 36 exiting from port 35 of the Y-body contains the optical fibers 39 for transmitting signals to and from the sensing means 34 at the distal end of the probe, and has an optical/electrical connector 38 at its distal end for connection via an optical/electrical line 40 to an automatic blood gas (ABG) monitor 44. The monitor has the appropriate excitation source, detector, filters and software for the type of sensor being used. A preferred monitor, for use with the lanthanide oxygen sensor described hereinafter, is described in U.S. Pat. No. 4,900,933 to Nestor et al. entitled "Excitation And Detection Apparatus For Remote Sensor Connected By Optical Fiber," the disclosure of which is hereby incorporated by reference in its entirety. The monitor 44 has a display screen 46 with graphical overlay 48 for presenting a continuous display of the partial pressures of oxygen ($O_2$) and carbon dioxide ($CO_2$), as well as pH, in graphical form. A digital display of these parameters may also be provided by monitor 44. A memory storage device 42 is provided at the proximal end of outer probe sheath 36 for connection to monitor 44, which memory device contains the calibration data, as described hereinafter.

Figure 3:
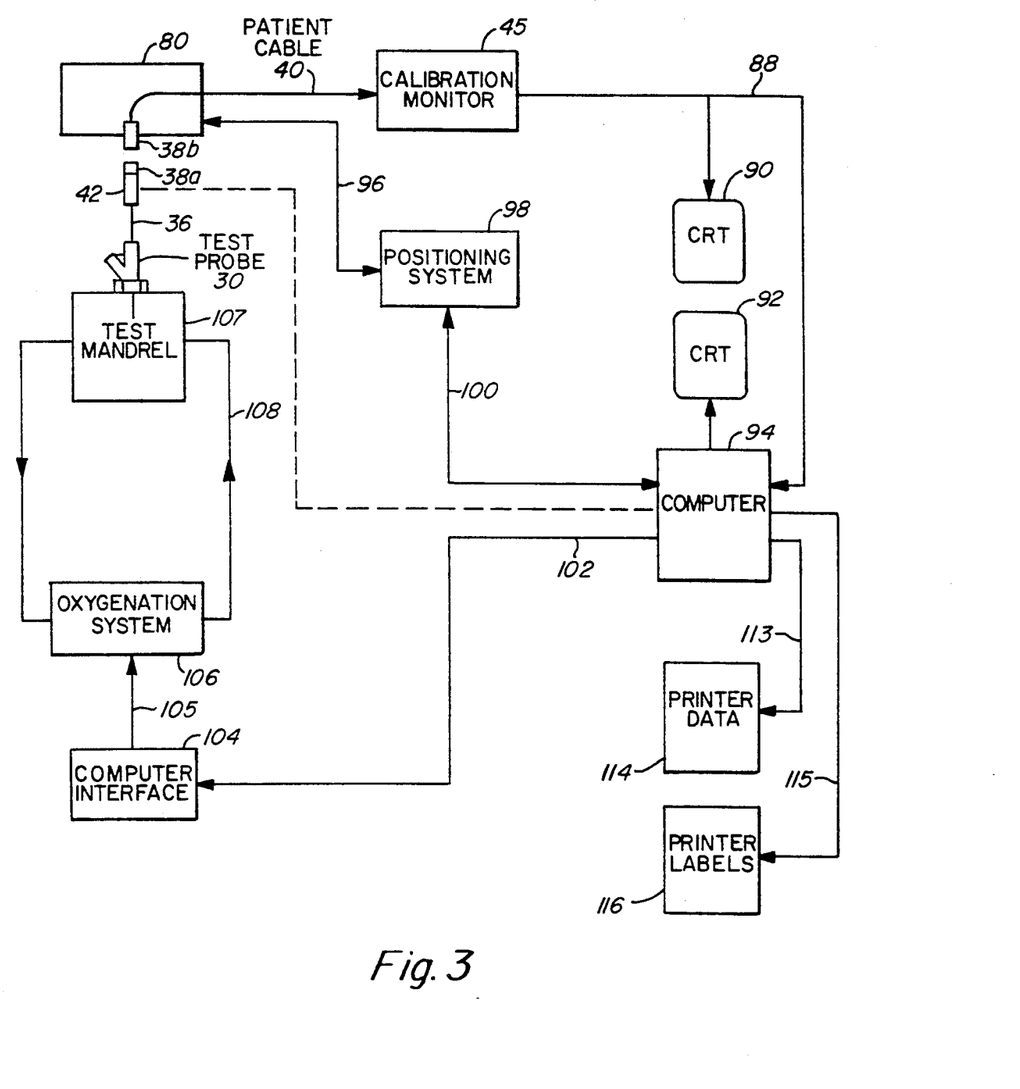
FIG. 3 is a diagram of the calibration apparatus.

The system for calibrating the probe 30 is illustrated in FIG. 3. As previously indicated, this calibration occurs at the manufacturing site, which eliminates the need for the user to purchase and use any calibration equipment.

The preferred calibration system is designed to calibrate a series of probes in a batch process. Thus, a test mandrel 107 in FIG. 3 accepts several probes, although only one test probe 30 is shown. A motorized positioning system 98 with a precision drive mechanism serially connects each of the test probes 30 to the patient cable 40 and calibration monitor 45. The calibration monitor 45 is similar to patient monitor 44 in having an appropriate excitation source, detector, filters and software for the type of sensor being used, such as the monitor described in U.S. Pat. No. 4,900,933. However, the calibration monitor has software adapted for making a series of four concentration measurements (one for each of the standard solutions), for each probe. The concentration data generated by calibration monitor 45 is sent to computer 94 which processes the same to generate a unique set of calibration coefficients for each probe. The calibration coefficients are represented by a series of ID values which may be electronically encoded in the memory device 42, or alternatively may be printed as labels 116 for application to the sensor package for manual entry into the blood gas monitor 44. An oxygenation system 106 which supplies the test mandrel 107 via closed loop 108 is likewise computer controlled, and is shown in greater detail in FIG. 4.

The calibration system is designed to operate automatically by having computer 94 control both the positioning system 98 via line 100, and the oxygenation system 106 via line 102, computer interface box 104 and line 105. The computer 94 receives a series of four concentration data values from each probe, one for each of four calibration solutions, and processes that data to generate a unique set of calibration coefficients. The coefficients are transferred to and stored in memory devices 42 and later introduced into blood gas monitor 44 for use of the probe in a patient. Alternatively, the calibration constants may be sent via line 115 to printer 116 for preparing labels which are attached to the sensor package, and/or via line 113 to printer 114 to print the values as data. In this alternative embodiment, the data would be manually input into the monitor 44 prior to use. An example of the method of calculating the unique calibration coefficients for a preferred example is described hereinafter.

The oxygenation system 106 (FIG. 4) of the calibration apparatus includes a series of four bubblers 130, designated A, B, C, and D, which supply four known calibration solutions in series to the test mandrel 107. In this example, the calibration solutions contain 5%, 15%, 21% and 40% $O_2$ respectively for generating a 4-point calibration curve for a blood oxygen sensor. The four sources of oxygen gas are designated 120 (A, B, C, and D) and are connected to each of four separate gas lines 122, gas line filters 124, manual flow meters 126, and valves 128, to the four bubblers 130. To the left of the bubblers 130 the system contains gas, whereas to the right of bubblers 130 a water solution having the respective gas concentration is fed through the closed loop 108. Input lines 132 and output lines 134 are connected to each bubbler 130. Each of bubblers 130 A, B, C, and D are alternatively connected to the test mandrel 107 by valves 138 and 139 on the solution side of the system, and pump 136 is further provided in each set of bubbler lines to regulate the flow. Water line flow meters 146 and water line filter 144 are also provided in loop 108 to regulate the flow of solution. In addition, an air flush and drain may be temporarily connected to the loop 108 by valves 140 and 142, respectively.

Figure 4:
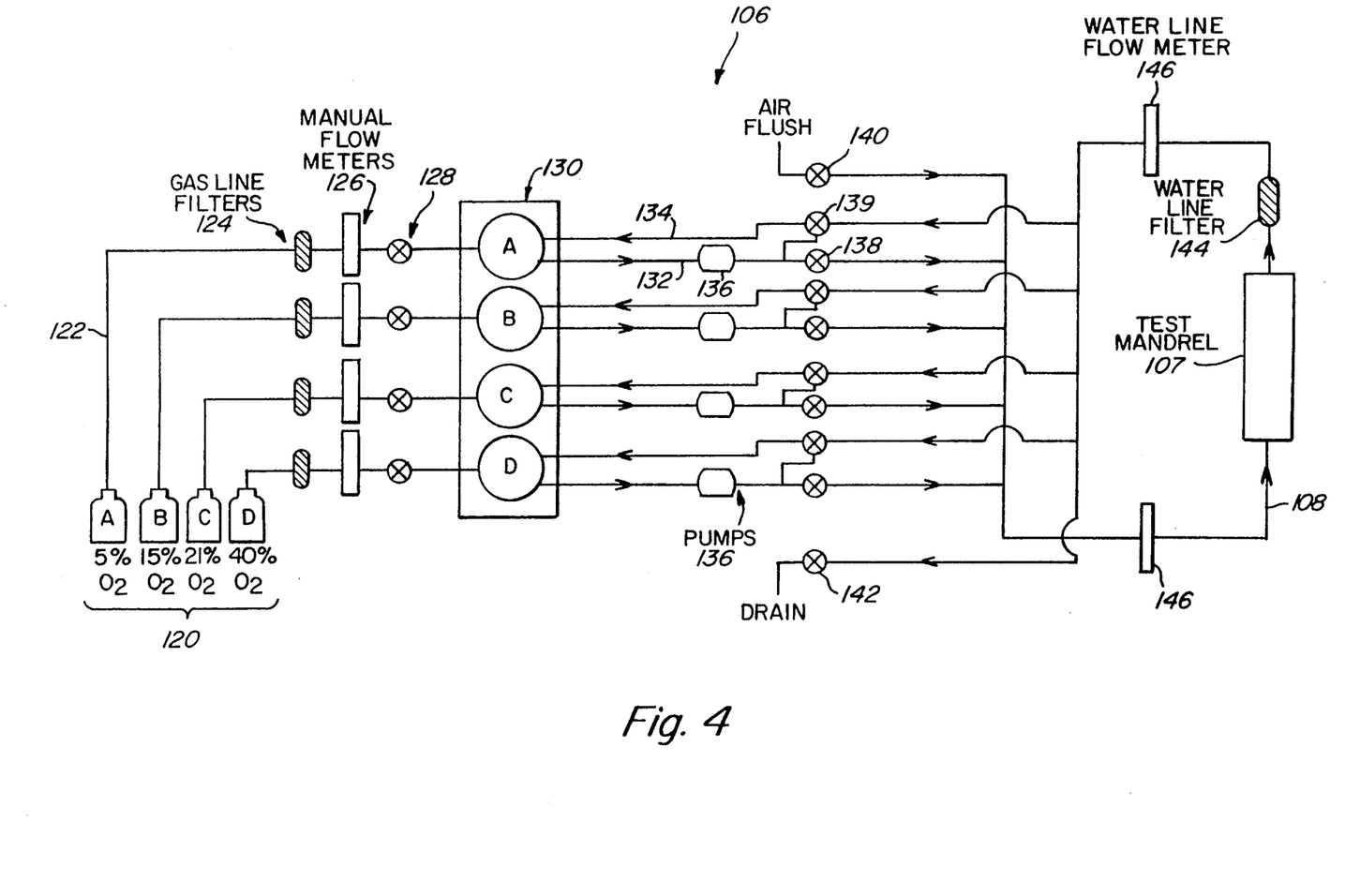
FIG. 4 is a diagram of an oxygenation system of the calibration apparatus.

During the calibration procedure, each of the four calibration solutions is serially connected to the test mandrel 107 to determine a calibration point for each of the test probes 30. For example, a 5% oxygen calibration solution is first provided via bubbler 130A by opening valves 128A, 138A and 139A and sufficient equilibriation time is allowed, e.g., 20 minutes, to allow the solution in loop 108 to stabilize at 5% $O_2$. A measurement is then taken for each of the test probes 30 by the calibration monitor 45, the probes being serially positioned by means of the positioning system 98 which mechanically places a stage 80, connected to patient cable 40 and monitor 45, adjacent each of the probes 30. As indicated in FIG. 3, the stage 80 is not required to contact each test probe, but rather an optical transmission occurs between the portions 38a and 38b of the connector between sheath 36 and patient cable 40. The light intensity response of the probe 30 being tested is determined by the calibration monitor 45 and an electronic signal corresponding to that value is transmitted on line 88 to computer 94. CRT displays 90 and 92 are connected to monitor 45 and computer 94 for monitoring the calibration data. The computer 94 sends an electronic positioning signal on line 100 to positioning system 98 to move the stage 80 (via line 96) to the next test probe.

After each of the test probes has been measured at the 5% calibration solution, the valves 128A, 138A and 139A are closed and valves 128B, 138B and 139B are opened so as to produce a second calibration solution of 15% $O_2$ at bubbler 130B. Again, following equilibration, each test probe is measured at this solution, before continuing on to calibration solutions C and D of 21 and 40% oxygen, respectively. After all of the probes have been measured with all four calibration solutions, the loop 108 may be flushed by opening flush valve 140 and drain valve 142.

The precalibrated system of this invention requires a sensor which is stable and thus for which the calibration data will not significantly change over a period of time, preferably at least about 24 hours. More preferably, the data remains accurate for a number of days, and more preferably a number of weeks. While the degree of accuracy will depend on the specific application, preferably the calibration data will change no more than ±15%, more preferably no more than ±10%, and still more preferably no more than ±5%.

A preferred oxygen sensor for use in this invention is described in U.S. Pat. No. 4,861,727 to Hauenstein et al., entitled "Luminescent Oxygen Sensor Based On A Lanthanide Complex," the disclosure of which is hereby incorporated by reference in its entirety. The preferred lanthanide complex, hereinafter referred to as Tb(SALAPPD), is formed of three terbium +3 ions, three hydroxides, and three Schiff base ligands of the formula 1:1 salicylaldehyde:2-amino1-phenyl-1,2-propanediol (SALAPPD). The oxygen-quenchable terbium complex Tb(SALAPPD) is combined with a non-oxygen quenchable europium complex Eu(SALAPPD), the later of which serves as a reference material to correct for system losses. Both complexes are disposed in solid solution in a polymeric matrix of poly(methyl methacrylate). The sensor body is formed at the distal tip of an optical fiber by dipping the distal end of the fiber in a solution of the polymeric matrix material, the oxygen quenchable lanthanide complex, and a non-oxygen quenchanble reference complex, and allowing the solvent to evaporate. A small polymeric bead of about 50–100 micrometers can be formed on a 100 micrometer diameter fiber. For example, the dipping solution may comprise about 2.5 grams of the Tb(SALAPPD) complex, 0.5 grams of the Eu(SALAPPD) complex, and 97.0 grams of poly(methyl methacrylate) dissolved in ethyl acetate at about 20% solids. The resulting body would thus have about 2.5% by weight of the terbium complex and 0.5% by weight of the europium complex. The terbium and europium complexes have a maximum excitation efficiency at 350–360 nm. The 547 nm emission peak for the terbium complex, and the 617 nm emission peak for the europium complex, are selected for maximum intensity and minimum overlap. The optical fiber is a commercially available silica fiber sold by Ensign Bickford Corp., 16 Ensign Drive, P.O. Box 1260, Avon, Conn.

It has been found that the preferred oxygen sensor based on the terbium and europium lanthanide complexes has a shelf life of at least about six months, between the time of calibration and the time of use (placement). The shelf life may in fact be considerably longer. Furthermore, the device remains stable after placement in the patient for at least about 72 hours. This is a substantial improvement over certain known invasive luminescent oxygen sensors which are generally understood to be composed of materials which are insufficiently stable to allow their calibration at any time other than immediately before their use, and which known devices generally remain stable in a patient (following placement) for a period of only 4–24 hours. Furthermore, the oxygen-sensitive lanthanide complexes used in this invention have an accuracy of ±10% for measuring an arterial oxygen partial pressure of 60–500 mm of mercury and an accuracy of ±5 mm in the range of arterial pressure of 30–60 mm of mercury.

An example illustrating the calibration procedure for this preferred oxygen sensor will now be described.

To calculate a unique set of sensor IDs for a specific oxygen probe, a series of light intensity readings of the terbium and europium complexes, designated $T_{sal}$ and $E_{sal}$, are collected at four different $pO_2$ levels. Then, using a best fit method, the coefficients for the quadratic equation:

$$Jt(pO_2)^2 + Kt(pO_2) + R\theta = R \tag{1}$$

are calculated. Then, from the coefficients Jt, Kt, and $R\theta$, the sensor IDs can be determined.

In general, a linear relationship between the light intensity values and $O_2$ concentration is desired so that a linear calibration curve can be determined for a specific probe. However, it was observed that with the preferred terbium lanthanide complex, the calibration line had a slight curve which was best fit by the designated quadratic equation (1). Furthermore, it was found that four calibration values gave a good "fit" of the curve to the data values, whereas two values would not be acceptable; while three values may be used, the accuracy would not be as good.

In this case, the following four calibration solutions were selected: 5% $O_2$, 15% $O_2$, 21% $O_2$ and 40% $O_2$. The middle two values were selected to cover the usual range of operation in a patient a healthy arterial blood oxygen value, which normally ranges between 15 and 21%. The lower range of 5% is near the minimum required to sustain life. The upper level of 40% corresponds to the arterial level in a patient being administered oxygen.

A series of four $T_{sal}$ values, one for each of the calibration solutions, and similarly four values of $E_{sal}$ values (for the europium complex) were measured.

The method of least squares was used to determine a best fit to quadratic equation (1) and thus determine the coefficients Jt, Kt and R$\theta$:

1. The method of least squares requires that the error, represented by $X^2$, between the actual data and the best fit be minimized. $X^2$ can be represented as follows:

$$X^2 = \Sigma \left( \frac{\Delta R_i}{\sigma_i} \right)^2 = \Sigma \left[ \frac{1}{\sigma_i^2} (R_i - R\theta - Kt^*pO_{2i} - Jt^*pO_{2i}^2)^2 \right]$$

where $R_i$ is the i-th measured value of the ratio of $E_{sal}/T_{sal}$, $\sigma_i$ is the standard deviation of the fit, and N is the number of measurements.

2. The minimum value of $X^2$ can be determined by setting the partial derivatives of $X^2$ to zero as follows:

$$\frac{\delta X^2}{\delta R\theta} = -2\Sigma \left[ \frac{1}{\sigma_i^2} (R_i - R\theta - Kt^*pO_{2i} - Jt^*pO_{2i}^2)^2 \right] = 0$$

$$\frac{\delta X^2}{\delta Kt} = -2\Sigma \left[ \frac{pO_{2i}}{\sigma_i^2} (R_i - R\theta - Kt^*pO_{2i} - Jt^*pO_{2i}^2) \right] = 0$$

$$\frac{\delta X^2}{\delta Jt} = -2\Sigma \left[ \frac{pO_{2i}^2}{\sigma_i^2} (R_i - R\theta - Kt^*pO_{2i} - Jt^*pO_{2i}^2) \right] = 0$$

3. The equations can be rearranged to the following (the factor $\sigma^2$ has been eliminated from the denominator of each term inside each summation sign for clarity):

$$\Sigma R_i = R\theta\Sigma 1 + Kt\Sigma pO_{2i} + Jt\Sigma pO_{2i}^2$$

$$\Sigma R_i^*pO_{2i} = R\theta\Sigma R_i + Kt\Sigma pO_{2i}^2 + Jt\Sigma pO_{2i}^3$$

$$\Sigma R_i^*pO_{2i}^2 = R\theta\Sigma pO_{2i}^2 + Kt\Sigma pO_{2i}^3 + Jt\Sigma pO_{2i}^4$$

4. Using determinant notation, the equations look like (the factor $\sigma^2$ has been eliminated from the denominator of each term inside each summation sign for clarity):

$$\begin{bmatrix} N & \Sigma pO_{2i} & \Sigma pO_{2i}^2 \\ \Sigma pO_{2i} & \Sigma pO_{2i}^2 & \Sigma pO_{2i}^3 \\ \Sigma pO_{2i}^2 & \Sigma pO_{2i}^3 & \Sigma pO_{2i}^4 \end{bmatrix} \begin{bmatrix} R\theta \\ Kt \\ Jt \end{bmatrix} = \begin{bmatrix} \Sigma R_i \\ \Sigma R_i^*pO_2 \\ \Sigma R_i^*pO_{2i}^2 \end{bmatrix}$$

5. Using Cramer's rule to solve the simultaneous equations (where det represents the determinant of the matrix; the factor $\sigma^2$ has been eliminated from the denominator of each term inside each summation sign for clarity):

$$\Delta = det \begin{bmatrix} N & \Sigma pO_{2i} & \Sigma pO_{2i}^2 \\ \Sigma pO_{2i} & \Sigma pO_{2i}^2 & \Sigma pO_{2i}^3 \\ \Sigma pO_{2i}^2 & \Sigma pO_{2i}^3 & \Sigma pO_{2i}^4 \end{bmatrix}$$

$$R\theta = \frac{1}{\Delta} det \begin{bmatrix} \Sigma R_i & \Sigma pO_{2i} & \Sigma pO_{2i}^2 \\ \Sigma R_i^*pO_{2i} & \Sigma pO_{2i}^2 & \Sigma pO_{2i}^3 \\ \Sigma R_i^*pO_{2i}^2 & \Sigma pO_{2i}^3 & \Sigma pO_{2i}^4 \end{bmatrix}$$

$$Kt = \frac{1}{\Delta} det \begin{bmatrix} N & \Sigma R_i & \Sigma pO_{2i}^2 \\ \Sigma pO_{2i} & \Sigma R_i^*pO_{2i} & \Sigma pO_{2i}^3 \\ \Sigma pO_{2i}^2 & \Sigma R_i^*pO_{2i}^2 & \Sigma pO_{2i}^4 \end{bmatrix}$$

$$Jt = \frac{1}{\Delta} det \begin{bmatrix} N & \Sigma pO_{2i} & \Sigma R_i \\ \Sigma pO_{2i} & \Sigma pO_{2i}^2 & \Sigma R_i^*pO_{2i} \\ \Sigma pO_{2i}^2 & \Sigma pO_{2i}^3 & \Sigma R_i^*pO_{2i}^2 \end{bmatrix}$$

The values for coefficients Jt, Kt and R$\theta$ are rounded as necessary to provide the desired accuracy.

The following equations are used to produce the ID #'s:

$$ID1 = 999^*((\log(min\_Jt) - \log(Jt))/(\log(min\_Jt) - \log(max\_Jt)))$$

$$ID2 = 999^*((\log(min\_Kt) - \log(Kt))/(\log(min\_Kt) - \log(max\_Kt)))$$

$$ID3 = 999^*((\log(min\_R\theta) - \log(R\theta))/(\log(min\_R\theta) - \log(max\_R\theta)))$$

The resulting ID numbers should then be rounded to integers between 0 and 999.

Using the calculated Jt, Kt, and R$\theta$ with the original Esal and Tsal counts, the $pO_2$'s are re-calculated using the equation:

$$pO_2 = \frac{-Kt + \sqrt{[Kt^2 - (4 * Kt * (R\theta - R))]}}{2 * Jt}$$

As a check on accuracy, the original $pO_2$ values of the gases are compared to the new calculated values. The absolute percentage errors for all four points together should add up in this example to less than 12% to be acceptable.

In addition, because the optical blood gas measurements vary with temperature, the temperature at which the measurement is taken must be accounted for. The calibration is conducted at 37° C., the temperature normally encountered in a patient's arterial blood. However, adjusted values for the coefficients Jt, Kt and R$\theta$ are inserted or stored in the monitor 44 for use in the event the blood oxygen measurement is taken at a temperature other than 37° C.

The three sensor ID values are sent to memory device 42 and stored in a memory chip, such as an electrically alterable read-only memory, a magnetic card, or the like. When the sensor probe is later attached to measuring monitor 44, the calibration information in the memory device 42 is automatically transferred to the monitor 44 and utilized to compute the displayed values of the blood parameters being measured.

Figure 5:
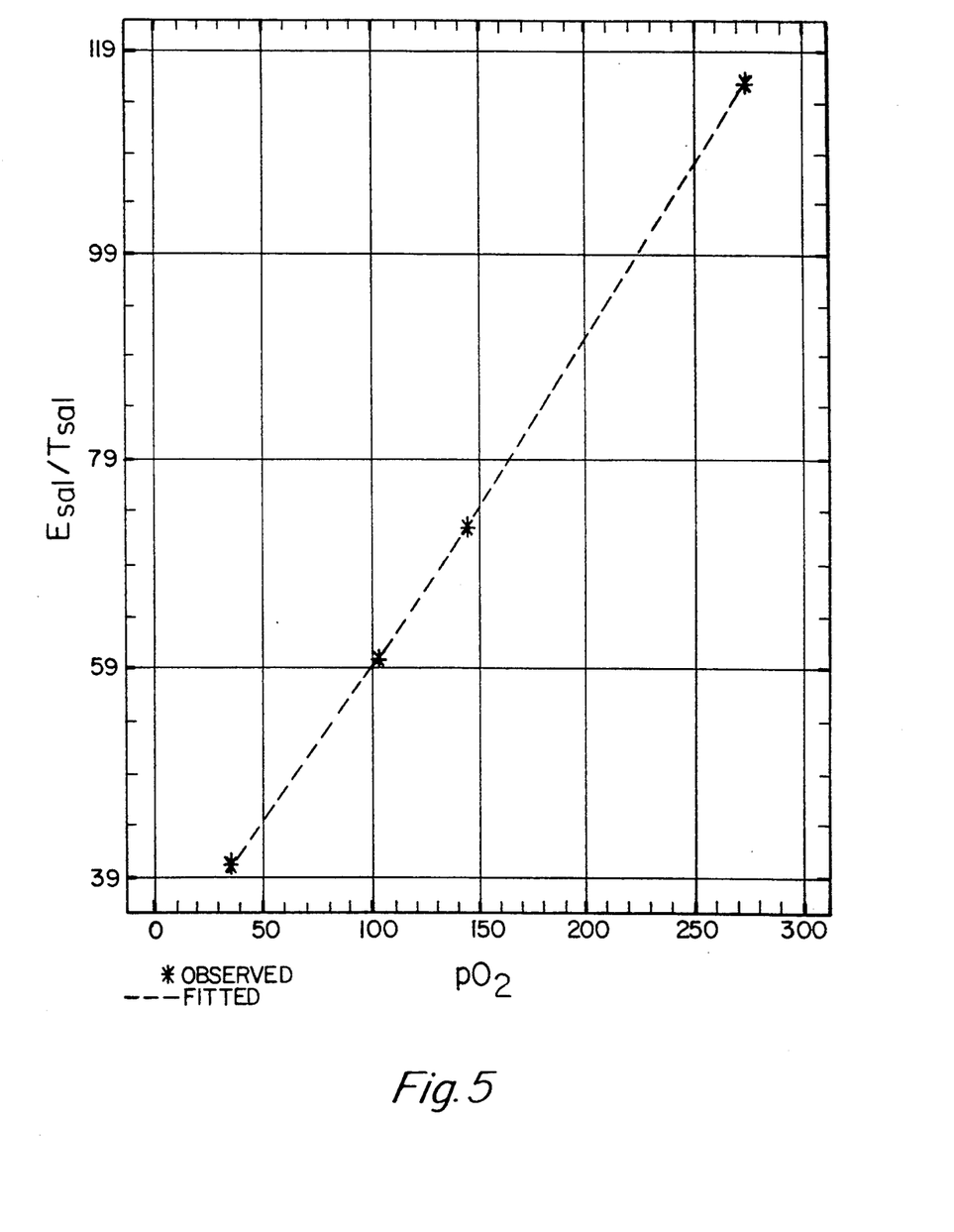
FIG. 5 is a graph of a computer generated curve of the calibration data.

FIG. 5 shows an example of a calibration curve (dashed line) generated by computer 94 from four measured values (designated by asterisks). The vertical axis represents the ratio of Esal/Tsal while the horizontal axis represents the value of the partial pressure of oxygen $pO_2$. A relatively close fit is obtained.

The lanthanide complex sensor used in this invention is preferably sterilized by means of a gaseous solution, and preferably an ethylene oxide (ETO) solution. The sensor may be placed on a polyethylene tray and covered with a gas permeable wrap such as Tyvek, sold by E. I. Dupont de Nemours, Wilmington, Del. The package is sealed and placed in a chamber while ETO is allowed to permeate through the wrap. The package sits in the chamber for about 24 hours, during which time all of the microbes are killed. The package is then removed from the chamber and the residual ETO gas is allowed to dissipate. Other types of sterilization procedures may be used with other sensors.

A preferred carbon dioxide sensor for use in this invention is described in U.S. Pat. No. 4,800,886 to Nestor et al. entitled "Sensor For Measuring The Concentration Of A Gaseous Component In A Fluid By Absorption," the disclosure of which is hereby incorporated by reference in its entirety. This patent describes an optical carbon dioxide sensor in which a solid body of polymeric material permeable to carbon dioxide is provided at the distal end of an optical fiber. An incident infrared signal transmitted down the fiber passes through the body, is reflected off the distal end of the body, and the intensity of the return signal is reduced in proportion to the concentration of carbon dioxide in the polymeric body. The body has a fixed length so that the path length over which energy is absorbed by the gaseous component is known and fixed. Because the fiber is not permeable to the gaseous component, it does not contribute to the path length along which absorption occurs. The path length is selected based upon the concentration to be measured and the absorption coefficient of the gaseous component in order to attain a readily detectable change in intensity for a change in concentration.

In a preferred embodiment, a single infrared transmitting fiber, such as a heavy metal fluoride (HMF) glass, is used. The solid cylindrical body of polymeric material is directly bonded to and coaxial with the distal end of the fiber, and preferably is made of silicone, which has a high value of carbon dioxide permeability and is substantially transparent at the absorption wavelength range (4.16 to 4.36 micrometers). A preferred material is the silicone adhesive sold under the designation MDX 4210, lot # HH 125429, by Dow-Corning Corp., Midland, Mich. A 2 mm path length (1 mm body length traversed twice) will absorb about 50–60% of the incident signal at 40 mm Hg $CO_2$. A reflective metal coating is provided at the distal end of the body, and a substantial portion of the outer surface of the body is also coated to preserve the light-guiding properties of the body.

The calibration procedure for the preferred carbon dioxide sensor is substantially the same as the described method for the oxygen sensor, but instead utilizes a number of calibration solutions having known $CO_2$ levels. Preferably, the $CO_2$ sensor will have an accuracy of ±5% over the entire operating range.

A pH sensor may also be provided on the probe. The calibration procedure for the pH sensor differs from that of the oxygen sensor in that no gases are provided in the calibration solutions. Rather, buffer solutions of known pH are circulated through the test mandrel.

While certain preferred embodiments of the invention have hereinbefore been described, it will be appreciated that variations and equivalents thereof will be perceived by those skilled in the art, which are nevertheless within the scope of the invention as defined by the claims appended hereto.

We claim:

1. A method of providing a precalibrated optical sensing system for sensing a parameter of blood, comprising the steps of:

providing a stable optical sensor in solid form for sensing a parameter of blood;

determining an associated set of calibration data for the sensor by exposing the sensor to at least one calibration medium, measuring the optical response of the sensor to the medium and determining the associated calibration data based on the response, and then removing the sensor from the calibration medium;

recording the calibration data; and sterilizing the sensor following calibration;

wherein the sensor may be stored at least 24 hours outside of any calibration medium and used along with recorded calibration data to sense a blood parameter without requiring recalibration prior to use.

2. A method of sensing a parameter of blood comprising the steps of:

providing a stable optical sensor in solid form for sensing a parameter of blood;

determining an associated set of calibration data for the sensor by exposing the sensor to at least one calibration medium, measuring the optical response of the sensor to the medium and determining the associated calibration data based on the response, and then removing the sensor from the calibration medium;

recording the calibration data;

sterilizing the sensor prior to use;

storing the sensor for at least 24 hours; and using the sensor and recorded calibration data to sense a parameter of blood.

3. The method of claim 1, wherein the sensor is used to sense a parameter selected from the group consisting of oxygen, carbon dioxide and pH.

4. The method of claim 1, wherein multiple sensors are provided to sense different parameters selected from the group consisting of oxygen, carbon dioxide and pH.

5. The method of claim 2, wherein the sensor is provided with an oxygen-quenchable luminescent lanthanide complex and the sensor is used to sense oxygen.

6. The method of claim 5, wherein the complex is provided in a polymeric matrix at a distal end of an optical fiber and the sensor is used in vivo to sense oxygen.

7. The method of claim 1, wherein a carbon dioxide absorbing sensor is provided and used to sense carbon dioxide.

8. The method of claim 7, wherein the sensor is a solid polymer body of fixed length disposed at the distal end of an optical fiber and the sensor is used in vivo to sense carbon dioxide.

* * * * *

UNITED STATES PATENT AND TRADEMARK OFFICE
CERTIFICATE OF CORRECTION

PATENT NO. : 5,234,835
DATED : August 10, 1993
INVENTOR(S) : Nestor, et. al.

It is certified that error appears in the above-indentified patent and that said Letters Patent is hereby corrected as shown below:

Col. 7, line 59 -  after "amino" insert -- - --.

Col. 8, line 66 -  after "patient" insert -- having --.

Signed and Sealed this

Fifteenth Day of March, 1994

Attest:

BRUCE LEHMAN

Attesting Officer

Commissioner of Patents and Trademarks